United States Patent [19]
Reiffenrath et al.

[11] Patent Number: 5,494,606
[45] Date of Patent: * Feb. 27, 1996

[54] 1,3-DIOXANE DERIVATIVES, AND LIQUID-CRYSTALLINE MEDIUM

[75] Inventors: Volker Reiffenrath, Rossdorf; Joachim Krause, Dieburg; Reinhard Hittich, Modautal; Eike Poetsch, Mühltal; Herbert Plach, Darmstadt, all of Germany

[73] Assignee: Merck Patent Gesellschaft Mit Beschrankter Haftung, Darmstadt, Germany

[*] Notice: The portion of the term of this patent subsequent to Oct. 19, 2010, has been disclaimed.

[21] Appl. No.: 67,155

[22] Filed: May 26, 1993

Related U.S. Application Data

[63] Continuation of Ser. No. 679,072, Jun. 20, 1991, abandoned.

[30] Foreign Application Priority Data

Apr. 26, 1990 [DE] Germany .................. 40 13 242.0

[51] Int. Cl.⁶ ..................... C09K 19/34; C07D 319/06
[52] U.S. Cl. ..................... 252/299.610; 549/369
[58] Field of Search .............. 252/299.61; 549/369

[56] References Cited

U.S. PATENT DOCUMENTS

| | | | |
|---|---|---|---|
| 4,332,354 | 3/1982 | Sorkin | 252/299.61 |
| 4,335,012 | 6/1982 | Sorkin | 252/299.61 |
| 4,414,131 | 11/1983 | Sethofer et al. | 252/299.1 |
| 4,512,636 | 4/1985 | Andrews et al. | 359/103 X |
| 4,551,264 | 11/1985 | Eidenschunk et al. | 252/299.62 |
| 4,565,425 | 1/1986 | Petrzilka et al. | 359/103 X |
| 4,630,897 | 12/1986 | Andrews et al. | 359/103 X |
| 4,659,502 | 4/1987 | Fearon et al. | 252/299.61 |
| 4,676,604 | 6/1987 | Petrzilka | 359/103 X |
| 4,704,227 | 11/1987 | Krause et al. | 252/299.61 |
| 4,709,030 | 11/1987 | Petrzilka et al. | 544/242 |
| 4,755,323 | 7/1988 | Eidenschunk et al. | 252/299.61 |
| 4,871,469 | 10/1989 | Reiffenrath et al. | 252/299.61 |
| 4,886,619 | 12/1989 | Janulis | 252/299.1 |
| 4,886,621 | 12/1989 | Sage et al. | 252/299.61 |
| 5,013,478 | 5/1991 | Petrzilka | 252/299.63 |
| 5,026,879 | 6/1991 | Obikawa | 549/369 |
| 5,032,313 | 7/1991 | Goto et al. | 252/299.63 |
| 5,082,587 | 1/1992 | Janulis | 252/299.01 |
| 5,230,829 | 7/1993 | Bartmann et al. | 252/299.63 |
| 5,254,698 | 10/1993 | Coates et al. | 549/369 |

FOREIGN PATENT DOCUMENTS

| | | | |
|---|---|---|---|
| 0315014 | 5/1989 | European Pat. Off. | |
| 3405914 | 8/1985 | Germany | 549/370 |

*Primary Examiner*—Cynthia Harris
*Attorney, Agent, or Firm*—Millen, White, Zelano, & Branigan

[57] ABSTRACT

Novel 1,3-dioxane derivatives of the formula I

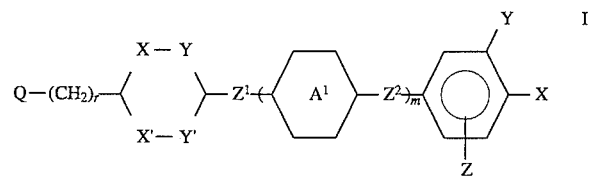

in which
Q is $CHalogen_lH_{3-l}$, $C_nH_{2n+1}$—O— or $C_2H_{2n+1}$—CH=CH—, where
Halogen is F or Cl,
l is 1, 2 or 3 and
n is 0 to 5,
r is 0 to 5,
$X=X'=O$ and $Y=Y'=CH_2$ or
$X=X'=CH_2$ and $Y=Y'=O$,
$Z^1$ and $Z^2$ are each, independently of one another, —$C_2H_4$— or a single bond,
$A^1$ is trans-1,4-cyclohexylene, 1,4-phenylene, 3-fluoro-1,4-phenylene or 3,5-difluoro-1,4-phenylene,
m is 0, 1 or 2,
X is F, Cl, —$CF_3$, —CN, —$OCF_3$ or —$OCHF_2$ and
Y and Z are each, independently of one another, H or F, can be used as components of liquid-crystalline media.

12 Claims, No Drawings

1,3-DIOXANE DERIVATIVES, AND LIQUID-CRYSTALLINE MEDIUM

This application is a continuation of application Ser. No. 07/679,072, filed Jun. 20, 1991, abandoned.

The invention relates to novel 1,3-dioxane derivatives of the formula I

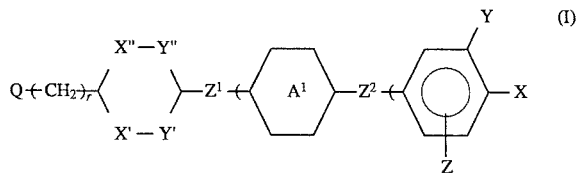

in which
Q is $C(Hal)_pH_{3-p}$, $C_nH_{2n+1}$—O— or $C_nH_{2n+1}$—CH=CH—, where
Halogen is F or Cl,
p is 1, 2 or 3 and
n is 0 to 5,
r is 0 to 5,
X"=X'=O and Y"=Y'=$CH_2$ or
X"=X'=$CH_2$ and Y"=Y'=O,
$Z^1$ and $Z^2$ are each, independently of one another, —$C_2H_4$— or a single bond,
$A^1$ is trans-1,4-cyclohexylene, 1,4-phenylene, 3-fluoro-1,4-phenylene or 3,5-difluoro-1,4-phenylene,
m is 0, 1 or 2,
X is F, Cl, —$CF_3$, —CN, —$OCF_3$ or —$OCHF_2$ and
Y and Z are each, independently of one another, H or F.

DE-A 29 44 905 discloses liquid crystals of the formula

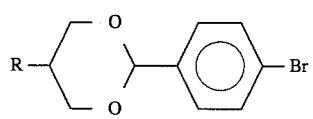

($R=C_6H_{13}$ or $C_8H_{17}$).

However, compounds of this type are not up to the high demands made of the electrical resistance, as required, for example, for displays having an active matrix. In addition, compounds of this type have fairly high values for the threshold voltage in liquid-crystalline media.

Like similar compounds, for example known from DE-A 26 36 684, the compounds of the formula I can be used as components of liquid-crystalline media, in particular for displays based on the principle of the twisted cell.

All the substances employed hitherto for this purpose have certain disadvantages, for example excessively high melting points, excessively low clearing points, inadequate stability to the action of heat, light or electrical fields, inadequate electrical resistance, unfavorable elastic properties, excessive temperature dependence of the threshold voltage or result in excessively high threshold voltages.

In particular in displays of the supertwist type (STN) having twist angles considerably greater than 220° C. or in displays having an active matrix, the materials employed hitherto have disadvantages.

The invention had the object of finding novel liquid-crystalline compounds which are suitable as components for liquid-crystalline media, in particular for nematic media having positive dielectric anisotropy, and which do not have the disadvantages of the known compounds, or only do so to a lesser extent. This object has been achieved by the provision of the novel compounds of the formula I.

It has been found that the compounds of the formula I are eminently suitable as components of liquid-crystalline media. In particular, they can be used to obtain liquid-crystalline media having broad nematic ranges, excellent nematogeneity down to low temperatures, excellent chemical stability, excellent elastic properties, pronounced $\epsilon^1$ with positive dielectric anisotropy, low threshold voltage, low temperature dependence of the threshold voltage and/or low optical anisotropy. In addition, the novel compounds have good solubility for other components of media of this type and high positive dielectric anisotropy at the same time as favorable viscosity.

The compounds of the formula I make it possible to produce STN displays having a very steep electro-optical characteristic line and displays having an active matrix and excellent long-term stability. Through a suitable choice of round n, the threshold voltages in displays of both types can be significantly reduced.

In the pure state, the compounds of the formula I are colorless and form liquid-crystalline mesophases in a temperature range which is favorably located for electrooptical use.

The invention thus relates to the compounds of the formula I and to the use of the compounds of the formula I as components of liquid-crystalline media, to liquid-crystalline media containing at least one compound of the formula I, and to electrooptical displays which contain media of this type.

Above and below, Q, r, X, Y, X', Y', $Z^1$, $Z^2$, $A^1$, X, Y, m and Z are as defined above, unless expressly stated otherwise.

In the compounds of the formula I, the alkylene groups $(CH_2)_r$ are preferably straight-chain. Accordingly, $(CH_2)_r$ is preferably methylene, ethylene, n-propylene, n-butylene or n-pentylene. m is preferably 0 or 1, particularly preferably 0. r is preferably 2, 3 or 4. r is furthermore preferably 1, in particular if Q=$C_nH_{2n+1}$—CH=CH—.

The radical

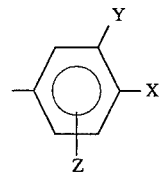

is preferably

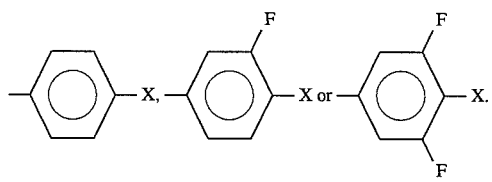

X is preferably F, Cl, —$CF_3$ or —$OCF_3$.

The following are preferred subformulae of the compounds according to the invention:

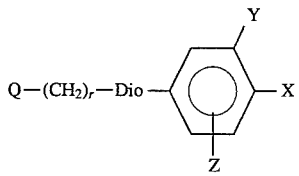

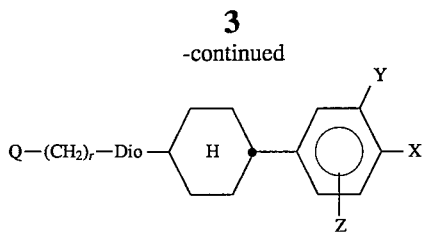

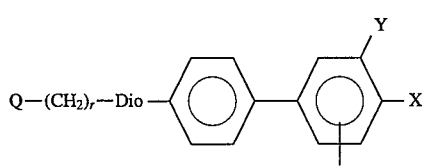

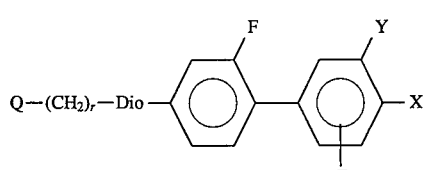

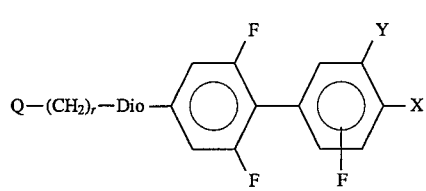

$Z^1$ and $Z^2$ are preferably single bonds or one of these groups is alternatively —$C_2H_4$—. m is preferably 0 or 1. However, compounds where m=2 (with $A^1$ and $Z^2$ identical to or different from one another) are furthermore preferred, in particular those of the subformulae below:

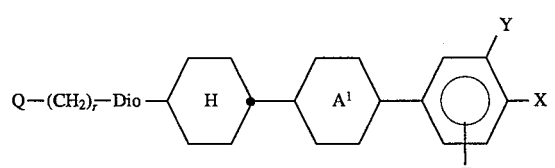

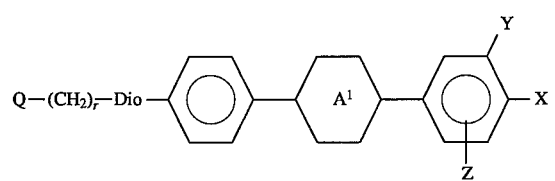

Particular preference is given to the compounds of the subformula Ia

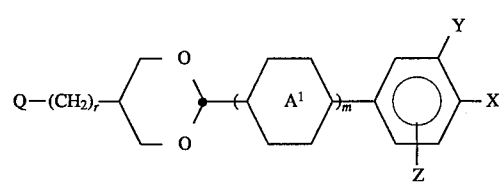

in which Q, r, $A^1$, m, X, Y and Z are as defined for the formula I. Z is preferably in the ortho-position to X. In a particularly preferred embodiment, Y=Z=F. $A^1$ is preferably trans-1,4-cyclohexylene. Q is preferably $CF_3$, $CHF_2$, $CH_2F$, $CH_2Cl$, $CH_3O$—, $CH_2$=CH— or $CH_3$—CH=CH—(trans). Halogen is preferably F.

In the above formulae, Dio is

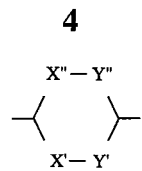

and is preferably

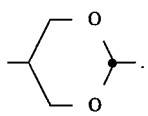

In addition, the compounds of the formula I are prepared by methods which are known per se, as described in the literature (for example in the standard works such as Houben-Weyl, Methoden der Organischen Chemie, [Methods of Organic Chemistry], Georg-Thieme-Verlag, Stuttgart) to be precise under reaction conditions which are known and suitable for the reactions mentioned. Use may also be made of variants which are known per se, but are not described here in greater detail.

If desired, the starting materials can also be formed in situ by not isolating them from the reaction mixture but instead immediately reacting them further to form the compounds of the formula I.

The 1,3-dioxane derivatives according to the invention are prepared in a manner which is conventional per se by condensation of 1,3-diols of the formula IIa with aldehydes of the formula IIIa or of 1,3-diols of the formula IIb with aldehydes of the formula IIIb:

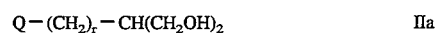

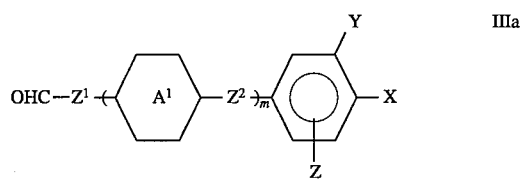

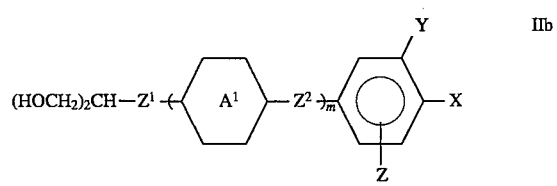

Some of the precursors of the formulae IIa, IIIa, IIb and IIIb are known. All these compounds can be prepared by routine methods, for example in accordance with the following synthesis scheme:

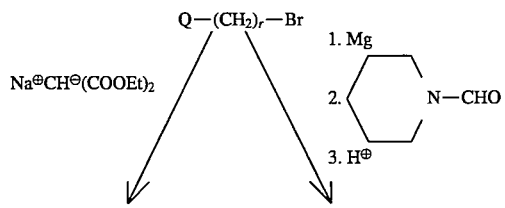

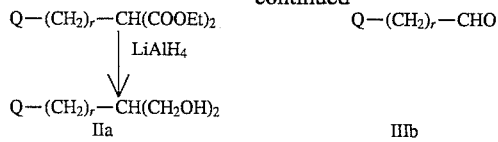

The compounds of the formulae IIIa and IIb can be prepared analogously. The synthesis of some particularly preferred compounds of the formula IIIa and IIb are described in greater detail below

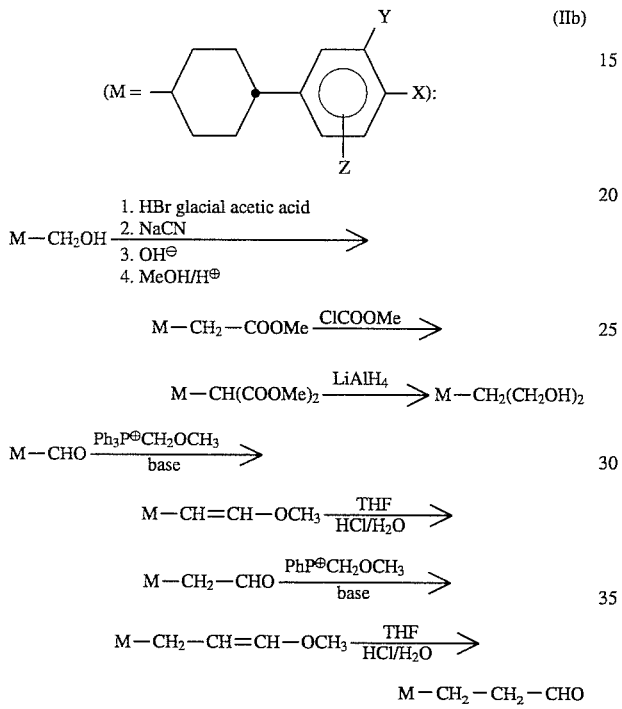

Furthermore, compounds of the formula IIIa can be obtained by transition metal-catalyzed cross-coupling reactions (E. Poetsch, Kontakte (Darmstadt) 1988 (2), p. 15), such as, for example:

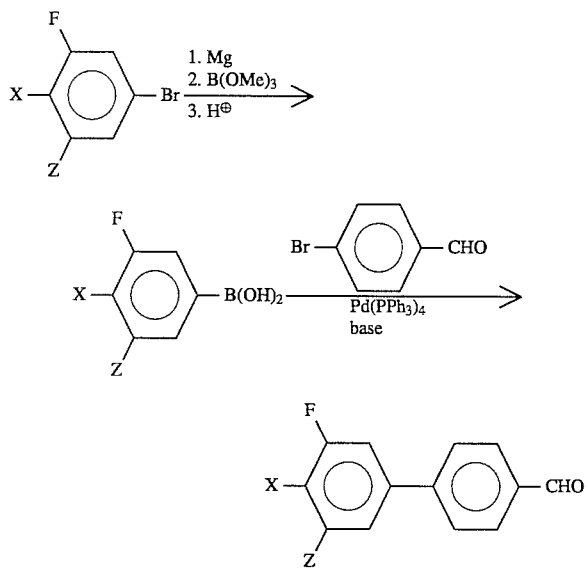

Precursors which are suitable for synthesis of the compounds of the formula I2 according to the invention can be obtained, for example, in accordance with the following synthesis scheme:

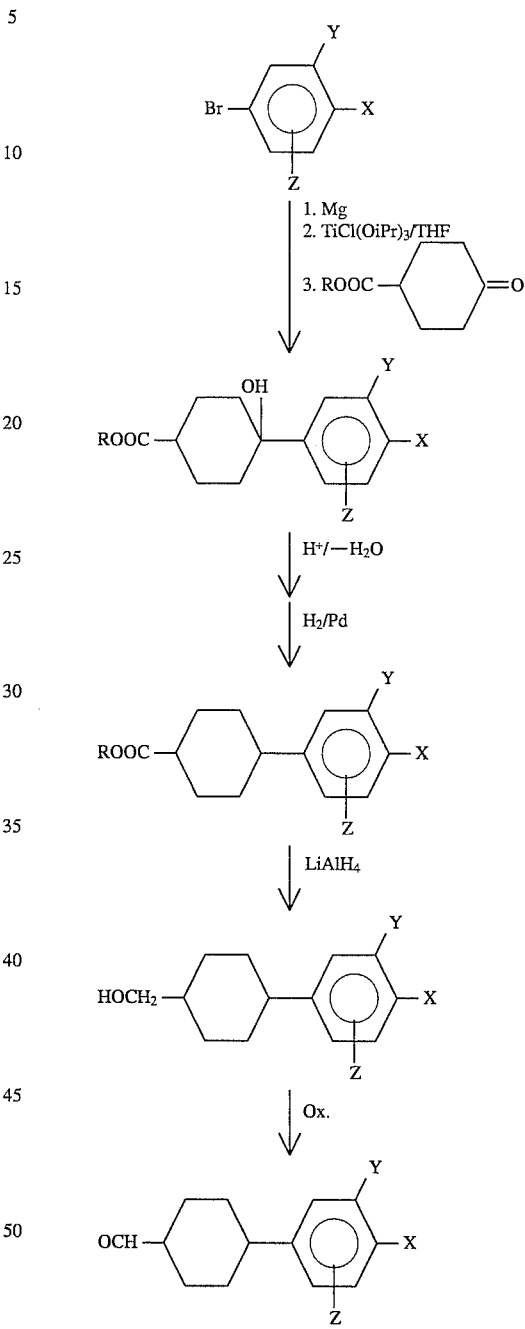

The Grignard compound obtained from the corresponding bromobenzene derivative is reacted with chlorotrialkyl orthotitanate or orthozirconate by the method of WO 87/05599 to give the tertiary cyclohexanol. Elimination of water, hydrogenation of the double bond and isomerization give, by customary methods, the transcyclohexane carboxylic acid ester. From the latter, conventional standard methods give the suitable aldehydes for the compounds according to the invention, which are obtainable from the latter by the Wittig synthesis and subsequent hydrogenation of the double bond.

Some of the bromobenzene derivatives used as starting materials are known, and some can be prepared without difficulties by standard methods of organic chemistry from compounds which are known from the literature. For example, the $OCF_3$ or $OCHF_2$ compounds can be obtained by known methods from the corresponding phenols and the $CF_3$ or CN compounds from the corresponding benzoic acids. Compounds of the formula

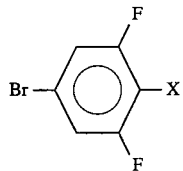

and corresponding monofluorinated compounds can be obtained, for example, from the known precursors where X=H by lithiation at low temperatures and subsequent reaction with a suitable electrophile.

The synthesis of a particularly preferred starting material of the formula IIIa' is described below:

the formula IIa are preferably obtained in accordance with the scheme below:

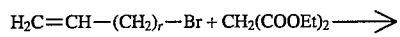

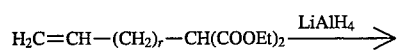

Particular preference is also given to compounds of the sub-formula

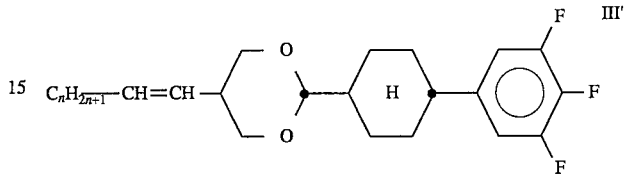

which can be prepared in accordance with the scheme below:

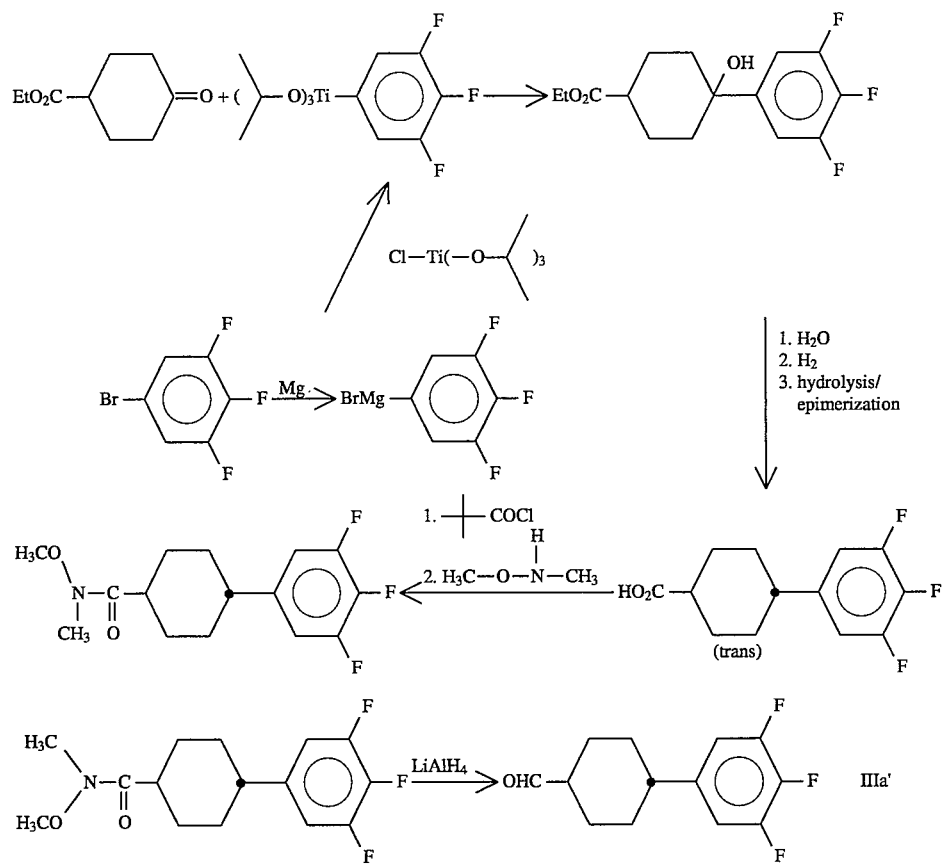

The condensation of this intermediate with compounds of the formula IIa gives preferred dioxane derivatives. Q is preferably $CH_2=CH-$. The corresponding compounds of

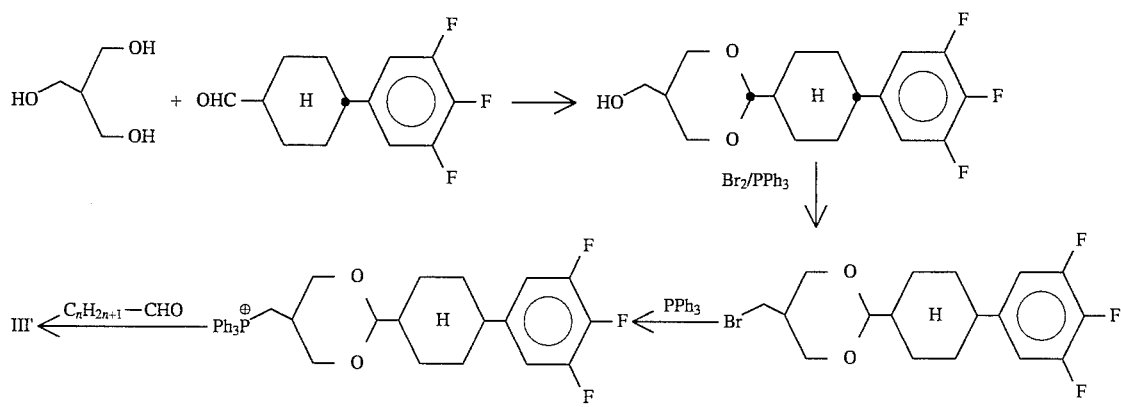

The malonic ester is alkylated in a known manner by generating its anion and reacting the latter with the alkenyl bromides. The reduction to the diols is carried out in a conventional manner by reduction using LiAlH$_4$. The condensation of the resultant diols with the aldehyde IIIa' is likewise carried out analogously to the formation of previously known dioxane systems by boiling equimolar amounts of the diol with the aldehyde in toluene on a water separator with addition of p-toluenesulfonic acid. The reaction is complete after only 4 hours.

The reaction product is purified by chromatography on silica gel and recrystallization from hexane. The synthesis of the aldehyde IIIa' required is also carried out by known methods.

Thus, 1-triisopropyloxytitanyl, 3,4,5-trifluorobenzene—prepared by transmetalation of 3,4,5-trifluorobenzenemagnesiumbromide using chlorotriisopropyloxytitanium— is reacted chemoselectively with ethyl cyclohexanone-4-carboxylate (1) on the carbonyl group to give ethyl 4-hydroxy-4(3,4,5-trifluorophenyl)cyclohexanecarboxylate. Elimination of water, catalytic hydrogenation over Pd/C, hydrolysis and epimerization using KOH/methanol give the pure trans 4-(3,4,5-trifluorophenyl)cyclohexanecarboxylic acid-(1). The latter is converted into the mixed anhydride using pivaloyl chloride and, using N,O-dimethylhydroxylamine, into the corresponding amide. The latter is reduced in high yield using LiAlH$_4$ to give the aldehyde IIIa'.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes and tolans.

The 1,4-phenylene groups in these compounds may also be fluorinated.

The most important compounds suitable as further constituents of media according to the invention can be characterized by the formulae 1, 2, 3, 4 and 5:

| R'-L-E-R" | 1 |
|---|---|
| R'-L-COO-E-R" | 2 |
| R'-L-OOC-E-R" | 3 |
| R'-L-CH$_2$CH$_2$-E-R" | 4 |
| R'-L-CC-E-R" | 5 |

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group comprising -Phe-Cyc-, -Cyc-Cyc-, -G-Phe- and -G-Cyc-.

In the compounds of the sub-formulae 1a, 2a, 3a, 4a and 5a, R' and R" are in each case, independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl. In the compounds of the sub-formulae 1b, 2b, 3b, 4b and 5b, R" is —CN, —CF$_3$, —OCF$_3$, F, Cl or -NCS; in this case, R has the meaning given for the compounds of the sub-formulae 1a to 5a and is preferably alkyl or alkenyl. R" is particularly preferably selected from the group comprising -F, Cl, CF$_3$ and —OCF$_3$. However, other variants of the proposed substituents in the compounds of the formulae 1, 2, 3, 4 and 5 are also common.

Many such substances or alternatively mixtures thereof are commercially available. All these substances can be obtained by methods which are known from the literature or analogously thereto.

Substances may be added to modify the dielectric anisotropy, the viscosity and/or the orientation of the nematic phases.

The examples below are intended to illustrate the invention without representing a limitation. m.p.= melting point, c.p.=clearing point. Above and below, percentages are percent by weight; all temperatures are indicated in degrees Celsius. "Customary work-up" means that water is added, the mixture is extracted with methylene chloride, and the organic phase is separated off, dried and evaporated, and the product is purified by crystallization and/or chromatography.

In addition, the abbreviations have the following meanings: C: crystalline-solid state, S: smectic phase (the index characterizes the phase type), N: nematic state, Ch: cholesteric phase, I: isotropic phase. The number between two symbols indicates the conversion temperature in degrees Celsius.

| DAST | diethylaminosulfur trifluoride |
|---|---|
| DCC | dicyclohexylcarbodiimide |
| DDQ | dichlorodicyanobenzoquinone |
| DIBALH | diisobutylaluminum hydride |
| DMSO | dimethyl sulfoxide |
| POT | potassium tertiary-butanolate |
| THF | tetrahydrofuran |
| pTSOH | p-toluenesulfonic acid |

EXAMPLE 1

A mixture of 0.1 m of 2-(3-fluoropropyl)- 1,3-propanediol, 0.1 m of p-(3,4-difluorophenyl)benzaldehyde (prepared by cross-coupling as described above), 1 g of p-toluenesulfonic acid and 200 ml of toluene is boiled for 1 hour on a water separator. Extractive work-up and purification by crystallization and chromatography give trans-2-(3,4-difluorobiphenyl-4'-yl)-5-(3-fluoropropyl)- 1,3-dioxane.

EXAMPLE 2

Trans-2-(4-fluorobiphenyl-4'-yl)-5-(3,3,3-trifluoropropyl)- 1,3-dioxane is obtained analogously to Example 1 by reaction of 2-(3,3,3-trifluoropropyl)- 1,3-propanediol with p-(p-fluorophenyl)benzaldehyde [from p-(p-fluorophenyl)bromobenzene by reaction with BuLi, N-formylpiperidine and acid].

EXAMPLE 3

Trans-2-(4-fluorophenyl)-5-(4-oxapentyl)- 1,3-dioxane is obtained analogously to Example 1 by reaction of 2-(4-oxapentyl)-1,3-propanediol with p-fluorobenzaldehyde.

The preferred compounds below are prepared analogously to or by the above synthesis schemes (X=X'=CH$_2$, Y=Y'=O, Z$^1$=Z$^2$=single bond, A$^1$= trans-1,4-cyclohexylene, m=1):

| Q | r | X | Y | Z* |
|---|---|---|---|---|
| H$_2$C=CH— | 0 | F | F | F |
| H$_2$C=CH— | 1 | F | F | F |
| H$_2$C=CH— | 2 | F | F | F |
| CH$_3$CH=CH— | 0 | F | F | F |
| CH$_3$CH=CH— | 1 | F | F | F |
| CH$_3$CH=CH— | 2 | F | F | F |
| CF$_3$ | 1 | F | F | F |
| CF$_3$ | 2 | F | F | F |
| CF$_3$ | 3 | F | F | F |
| CF$_3$ | 4 | F | F | F |
| CF$_3$ | 5 | F | F | F |
| CHF$_2$ | 2 | F | F | F |
| CHF$_2$ | 3 | F | F | F |
| CHF$_2$ | 4 | F | F | F |
| CHF$_2$ | 5 | F | F | F |
| CH$_3$O | 2 | F | F | F |
| CH$_3$O | 3 | F | F | F |
| CH$_3$O | 4 | F | F | F |
| CH$_3$O | 5 | F | F | F |

We claim:

1. A 1,3-dioxane derivative of the formula I

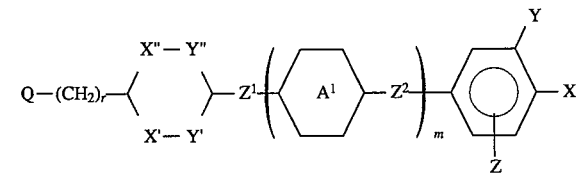

in which

Q is CHal$_p$H$_{3-p}$— or C$_n$H$_{2n+1}$—O—, where Hal is or Cl, p is 1, 2 or 3, n is 1 to 5, and r is 0 to 5; or Q is C$_n$H$_{2n+1}$—CH=CH—, and r is 0 or 1;

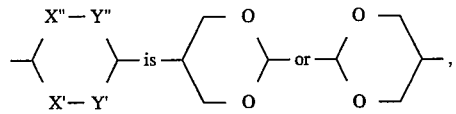

Z$^1$ and Z$^2$ are each independently of one another, —C$_2$H$_4$— or a single bond, A$^1$ is trans-1,4-cyclohexylene, 1,4-phenylene, 3-fluoro- 1,4-phenylene or 3,5-difluoro-1,4-phenylene, m is 0, 1 or 2, X is F, Cl, OCF$_3$ or OCHF$_2$, Y is F and Z is H.

2. The 1,3-dioxane derivative of claim 1, having the formula Ia

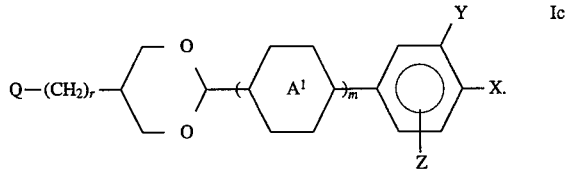

3. The 1,3-dioxane derivative of claim 2, wherein Q is CH$_2$Hal, OCH$_3$, —CH=CH$_2$ or —CH=CH—CH$_3$.

4. The 1,3-dioxane derivative of claim 1, having one of the formulae I1 to I5

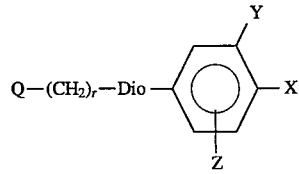

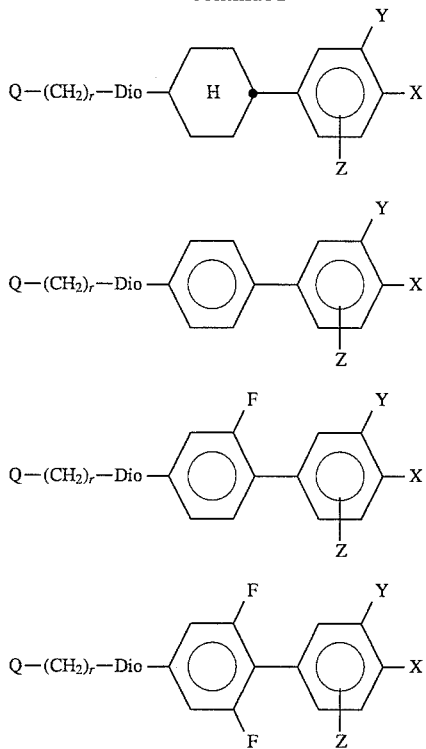

wherein Dio is

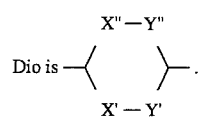

5. The 1,3-dioxane derivative of claim 1, wherein m is 2.

6. The 1,3-dioxane derivative of claim 1, having one of the formulae I6 and I7

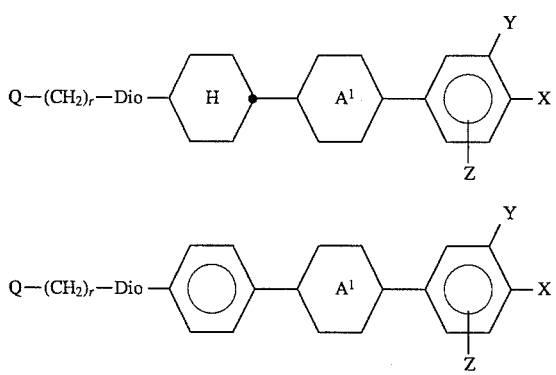

wherein Dio is

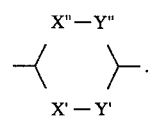

7. The 1,3-dioxane derivatives according to claim 1, wherein

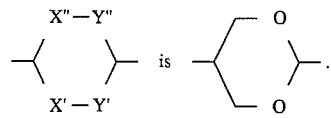

8. A liquid-crystalline medium for electrooptical displays containing at least two liquid-crystalline components wherein at least one component is a 1,3-dioxane derivative of the formula I of claim 1.

9. An electrooptical display comprising a liquid-crystal cell, wherein the liquid-crystal cell contains the medium of claim 8.

10. A liquid-crystalline medium for electrooptical displays comprising, as at least one component, at least one 1,3-dioxane derivative of the formula I of claim 1.

11. The 1,3-dioxane derivative of claim 1, wherein X is Cl.

12. A 1,3-dioxane derivative of the formula I

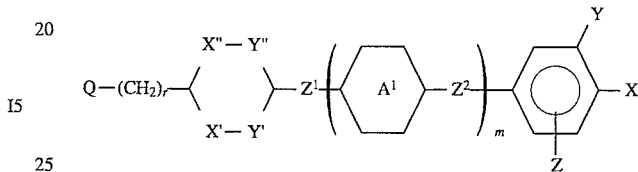

in which

Q is $CHal_pH_{3-p}$— or $C_nH_{2n+1}$—O—, where Hal is F or Cl, p is 1, 2 or 3, n is 1 to 5 and r is 0 to 5; or Q is $C_nH_{2n+1}$—CH=CH—, n is 0 to 5, and

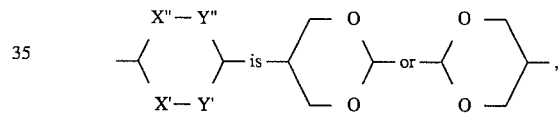

$Z^1$ and $Z^2$ are each independently of one another, —$C_2H_4$— or a single bond, $A^1$ is trans-1,4-cyclohexylene, 1,4-phenylene, 3-fluoro-1,4-phenylene or 3,5-difluoro-1,4-phenylene, m is 0, 1 or 2, X is F, Cl, $OCF_3$ or $OCHF_2$, and

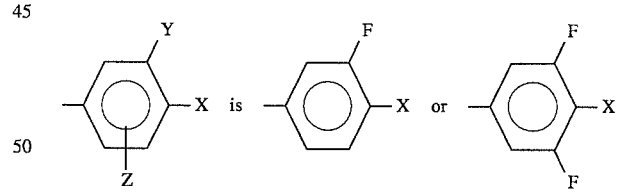

with the proviso that

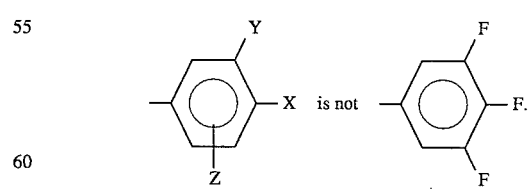

* * * * *